United States Patent [19]

Adams et al.

[11] Patent Number: 5,000,967

[45] Date of Patent: Mar. 19, 1991

[54] PROCESS FOR ENZYME PEELING OF FRESH CITRUS FRUIT

[75] Inventors: Bruce Adams, Pomona; William Kirk, Alta Loma, both of Calif.

[73] Assignee: Sunkist Growers, Inc., Ontario, Calif.

[21] Appl. No.: 340,278

[22] Filed: Apr. 19, 1989

[51] Int. Cl.$^5$ .............................................. A23L 1/212
[52] U.S. Cl. ........................................ 426/50; 426/52; 426/616; 426/287; 426/482
[58] Field of Search ................. 426/50, 287, 616, 482, 426/52

[56] References Cited

U.S. PATENT DOCUMENTS 1,601,027  9/1926  Lefevre et al. ...................... 426/287
3,347,678 10/1967  Villadsen et al. ..................... 426/50
4,284,651  8/1981  Bruemmer ............................ 426/50

OTHER PUBLICATIONS

Bruemmer, Joseph H. and Griffin, Alicia W., "Sectioning Grapefruit by Enzyme Digestion," *Proc. Fla. State Hort. Soc. 91*, 1978, pp. 112–114.

*Primary Examiner*—Marianne Cintins
*Attorney, Agent, or Firm*—Pretty, Schroeder, Brueggemann & Clark

[57] ABSTRACT

An improved process for preparing individual fruit sections from fresh citrus fruit, with improved ease of peeling and sectioning and with reduced amounts of adhering albedo. The fresh citrus fruit are initially scored so as to penetrate the albedo layer, but not the underlying juice sections, and the scored fruit is then immersed in an aqueous solution of a pectinase enzyme. A series of positive pressure pulses is applied to the immersed fruit, to infuse the enzyme solution into the albedo and, after storing the infusion-treated fruit for a prescribed time period, the peel and other membrane material can be readily removed from the fruit and the individual fruit segments readily separated from each other. Infusing the pectinase enzyme solution under pressure, rather than vacuum, and maintaining the solution at approximately room temperature, rather than an elevated temperature, significantly improves the ease of peeling and sectioning and reduces the amount of adhering albedo.

14 Claims, No Drawings

PROCESS FOR ENZYME PEELING OF FRESH CITRUS FRUIT

BACKGROUND OF THE INVENTION

This invention relates generally to processes for peeling fresh citrus fruit and, more particularly, to such processes that utilize the infusion of a pectinase enzyme into the fruit.

An example of a pectinase enzyme-infusion process of this particular kind is described in U.S. Pat. No. 4,284,651 to Bruemmer. In the described process, washed citrus fruit such as oranges and grapefruit are initially heated to a surface temperature of about 40 to 60 degrees C. and a core temperature of about 20 to 40 degrees C., after which the peel surface of the fruit is scored so as to penetrate the fruit's albedo or white layer, but not penetrate the fruit's juice segments. An aqueous solution of a pectinase enzyme is then vacuum infused into the fruit's albedo, at a vacuum of about 25 to 30 inches of mercury. After incubating the fruit for a period of 15 minutes to two hours, at a temperature of about 30 to 60 degrees C., the peel and other membrane material is removed from the fruit and the exposed fruit segments are separated from each other, with most of the segment membranes remaining intact. The fruit segments can then be refrigerated for extended durations, while retaining a fresh fruit flavor and appearance.

Although the process described briefly above has proven to be generally satisfactory in providing individual fruit segments having a fresh fruit flavor and appearance, it is believed that the process can be improved upon in several respects. For example, it is believed that a still higher proportion of individual fruit segments can be separated without damaging the segment's membrane and with less adhered albedo. In addition, it is believed that the pectinase enzyme solution used in the process can be used in a way that reduces its tendency to rapidly break down and lose its effectiveness so that it can be used effectively with more than just a single batch of citrus fruit.

It should, therefore, be appreciated that there is a need for an improved process for enzyme peeling fresh citrus fruit, which is effective in providing a increased ease in peeling and reduced adhering albedo and which can utilize a particular batch of pectinase enzyme solution to process a greater number of fresh fruit. The present invention fulfills this need.

SUMMARY OF THE INVENTION

The present invention resides in a process for peeling fresh citrus fruit, in which a pectinase enzyme solution is infused into the fruit in a way that enables the peel to be removed and individual fruit segments to be separated from each other with fewer of the segments being damaged and/or carrying adhered albedo. The process of the invention achieves these improved results by processing the fresh fruit at a cooler temperature than was done in the past and/or by infusing the pectinase enzyme into the fruit using a positive pressure rather than a vacuum. In addition to providing a greater proportion of whole fruit segments, the process of the invention also facilitates use of the pectinase enzyme solution to process a greater number of fresh fruit, over an extended duration, thus significantly reducing processing costs.

More particularly, the process of the invention includes an initial step of maintaining the core and surface temperature of the fresh citrus fruit at a temperature of less than about 40 degrees C., and the peel surface of the fruit is broken (e.g., scored) so as to penetrate the fruit's albedo layer, but not its juice segments. An aqueous solution of pectinase enzyme is then pressure infused into the scored fruit, after which the fruit is stored at a temperature of less than about 30 degrees C. for a prescribed duration, to allow the pectinase to break down the pectin present in the albedo. The fruit peel can then be readily removed and the individual fruit segments readily separated from each other, with a large proportion of the fruit segments remaining completely intact.

In a more detailed feature of the invention, the citrus fruit are maintained at a temperature of about 20 degrees C. throughout the entire process. Maintaining the pectinase enzyme solution at this temperature ensures that it will retain its effectiveness for an extended time period, whereby the solution can be used repeatedly for multiple batches of fresh citrus fruit.

In another more detailed feature of the invention, the step of pressure infusing includes a step of applying a plurality of pressure pulses to the fruit. Each pressure pulse preferably has a pressure of about 20 to 40 p.s.i., relative and the pulses are separated from each other by periods having pressures of about 0 p.s.i., relative. In addition, the pressure pulses preferably have durations of about 15 seconds, with the periods between pulses preferably having durations of about 5 seconds, and about six to ten such pulses are applied.

Other features and advantages of the present invention will become apparent from the following description of the preferred processes, which illustrate, by way of example, the principles of the invention.

DESCRIPTION OF THE PREFERRED PROCESSES

The invention resides in a process for preparing individual fruit segments from fresh citrus fruit using an aqueous solution of a pectinase enzyme. The solution is infused into the albedo, or white layer, of the citrus fruit peel, to break down the pectin contained in the albedo and thereby to facilitate an easy removal of the peel and separating of the individual fruit segments. Pectinase is a natural product of mold growth and is approved for food use by the United States Food and Drug Administration. Pectinase is commonly used commercially in a variety of food applications, such as clarification and stabilization of fruit juices. The process of the invention can be used particularly effectively with Valencia and navel oranges, grapefruit, and lemons.

In an initial step of the process, the peel of a batch of fresh citrus fruit is scored or otherwise broken so as to barely penetrate the peel's thick albedo layer, but not to penetrate any of the underlying fruit segments or segment membranes. The fruit preferably are each scored into six substantially equal-sized wedge sections, extending from the stem to the blossom end. Many other ways of breaking the peel also are suitable, including scoring the peel with a single- or multiple-ring pattern or a spiral pattern, and even grating or randomly scratching the peel. The scored fruit are then placed in an aqueous solution of pectinase enzyme, preparatory to the infusion. NOVO Pectinex 5XL is one suitable pectinase enzyme, and it can be used at a concentration of 1,000 ppm (i.e., 1.0 milliliters per liter) in tap water.

In accordance with the invention, the pectinase enzyme solution is infused into the scored fruit using pressure infusion In particular, the fruit and solution are placed together in a pressure chamber and a series of positive pressure pulses is applied to the chamber. The pressure pulses preferably each have a pressure of about 20 to 40 p.s.i., relative, and a duration of about 15 seconds. The pressure pulses are separated from each other by periods of 0 p.s.i., relative, having durations of about 5 seconds each. About six to ten successive pulses are preferably applied. Pulsing the pressure is believed to cause the fruit peel to flex, which helps to work the enzyme solution throughout the peel. A medium-sized orange (size 113) typically will draw in about 30 milliliters of the enzyme solution.

The pectinase enzyme-infused fruit are then removed from the pressure chamber and placed into storage tubs for one to two hours. This allows the enzyme to break down the pectin in the fruit's albedo. The fruit peel can thereafter be readily removed with only minimal amounts of albedo clinging to the fruit sections. In addition, the fruit segments can be readily separated from each other without damaging the segment membranes. Because of the minimal damage to the segment membranes, the separated fruit segments can be stored under refrigeration for extended durations while retaining a fresh fruit appearance and flavor.

In another feature of the invention, enhanced results can be realized if the entire process is performed at temperatures substantially lower than in the past. In particular, it has been found that operating at substantially room temperature, i.e., about 20 degrees C., results in an improved ease in peeling and sectioning and in a reduced amount of adhering albedo. In addition, maintaining the pectinase enzyme solution at a temperature of about 20 degrees C. retards a breakdown of the enzyme so that it can thereafter be used for an extended time on additional batches of fresh citrus fruit. Typically, each batch of pectinase enzyme can be used effectively with nine to ten successive batches of fresh citrus fruit At higher temperatures, such as 45 degrees C. used in the past, the enzyme solution appears to provide little effectiveness upon reuse after about 30 minutes. Processing at the lower temperature of about 20 degrees C. therefore results in a substantial reduction in processing costs.

The improvements in peeling and sectioning of the fruit resulting from infusing the enzyme at a lower temperature and from infusing the enzyme under pressure, rather than vacuum, is shown by Examples 1-3, set forth below.

EXAMPLE 1

In this example, which corresponds generally with the process described in U.S. Patent No. 4,284,651 to Bruemmer, 28 size-88 navel oranges and 16 size-40 ruby grapefruit were washed and brought to a peel temperature roughly equal to room temperature, or 20 degrees C. The fruit peel was then scored into six equal sections, from stem to blossom end, and placed in a vacuum chamber. Included with the fruit in the vacuum chamber was a solution of 1000 ppm NOVO Pectinex 5XL enzyme in tap water. The solution temperature was maintained at 42 to 48 degrees C., with no pH adjustment. A vacuum of 27 to 30 inches of mercury was then applied to the fruit for a time period of two to three minutes.

Following the vacuum infusion treatment, the fruit were removed from the vacuum chamber and placed into a plastic storage tub for one to two hours, to allow the enzyme to break down the pectin in the albedo. The fruit were subsequently peeled by hand and exhibited only a fair degree of ease in peeling and sectioning and exhibited a significant amount of adhering albedo.

EXAMPLE 2

The same numbers and kinds of citrus fruit as were used in Example 1 were used in this example. The only difference between the process of Example 1 and that of this example was that the pectinase enzyme solution was maintained at a temperature of 20-22 degrees C., rather than 4214 48 degrees C. The fruit exhibited significantly improved ease in peeling and sectioning and a reduced amount of adhering albedo. What little albedo remained adhered could be readily stripped with a light brushing under a rinse.

EXAMPLE 3

In this example, the same numbers and kinds of citrus fruit as were used in Examples 1 and 2 were processed. The only difference between the process of this example and that of Example 2 was that the fruit and pectinase enzyme solution were placed in a pressure chamber, rather than a vacuum chamber, and a series of positive pressure pulses was applied. In particular, about ten successive 15-second pressure pulses of 30 p.s.i., relative, were applied, separated from each other by 5-second periods of 0 p.s.i., relative. The fruit processed in accordance with this example exhibited significantly improved ease in peeling and sectioning and a significantly reduced amount of adhering albedo.

The fruit processed in the processes of Examples 1, 2 and 3 were individually graded on a scale of 1 to 4 for peeling ease, lack of adhering albedo, and sectioning ease. A grade of 1 indicated good, 2 indicated moderately good, 3 indicated fair, and 4 indicated poor. The mean grades for navel oranges processed in accordance with the processes of Examples 1, 2 and 3 are indicated in Table 1, and the mean grades for ruby grapefruit processed in accordance with the same processes are indicated in Table 2. It will be noted that significant improvement in each category is provided by infusing the pectinase enzyme solution at 20 degrees C. (Example 2), as contrasted with 45 degrees C. (Example 1), and by infusing the solution under pressure (Example 3), rather than vacuum (Examples 1 and 2).

TABLE 1

| | Oranges | | |
|---|---|---|---|
| | Ease in Peeling | Lack of Adhering Albedo | Ease in Sectioning |
| Example 1 | 3.43 | 3.43 | 3.00 |
| Example 2 | 1.61 | 2.54 | 2.39 |
| Example 3 | 1.18 | 2.11 | 2.29 |

TABLE 2

| | Grapefruit | | |
|---|---|---|---|
| | Ease in Peeling | Lack of Adhering Albedo | Ease in Sectioning |
| Example 1 | 2.75 | 2.69 | 3.19 |
| Example 2 | 1.44 | 2.69 | 2.88 |
| Example 3 | 1.13 | 2.25 | 2.38 |

The effect that pressure magnitude has on the degree of infusion of the pectinase enzyme into the albedo is shown by Examples 4–7, set forth below.

EXAMPLE 4

The peels of 15 size-113 navel oranges were scored into six equal sections, from stem to blossom end, and the scored fruit were placed in a six-gallon pressure cooker. Included with the fruit in the pressure cooker was a solution of 500 ppm Rohm Tech D5L enzyme in tap water, at a temperature of about 26 degrees C. A constant pressure of about 10 p.s.i., relative, was then applied to the fruit and enzyme solution for a period of about two minutes.

Following the pressure treatment, the fruit were peeled and judged as to the percentage dry portion of the albedo, corresponding to the amount of albedo not infused with the enzyme solution. In the judging, a score of 1 indicated 0 percent dry albedo, 2 indicated 1–10 percent dry albedo, 3 indicated 10–30 percent dry albedo, 4 indicated 30–60 percent dry albedo, and 5 indicated 60–100 percent dry albedo. As set forth in Table 3 below, the fruit in this Example 4 were judged to have an average score of 3.47, indicating only a fair infusion of enzyme into the albedo was accomplished.

EXAMPLE 5

Fifteen size-113 navel oranges were processed in the same fashion as in Example 4, except that a pressure of about 20 p.s.i. was applied. As set forth in Table 3, the fruit in this Example 5 were judged to have a significantly reduced percentage of dry albedo, as compared with the fruit in Example 4.

EXAMPLE 6

Fifteen size-113 navel oranges were processed in the same fashion as in Examples 4 and 5, except that a pressure of about 30 p.s.i. was applied. As set forth in Table 3, the fruit were judged to have a percentage of dry albedo comparable to that of Example 5.

EXAMPLE 7

Fifteen size-113 navel oranges were processed in the same fashion as in Example 4–6, except that a pressure of about 40 p.s.i. was applied. As set forth in Table 3, the fruit were judged to have a percentage of dry albedo comparable to that of Examples 5 and 6.

TABLE 3

| Extent of Infusion | Score |
| --- | --- |
| Example 4 (10 p.s.i) | 3.47 |
| Example 5 (20 p.s.i) | 2.33 |
| Example 6 (30 p.s.i) | 2.20 |
| Example 7 (40 p.s.i) | 2.20 |

It should be appreciated from the foregoing description that the present invention provides an improved process for preparing individual fruit segments from fresh citrus fruit, with improved ease of peeling and sectioning and with reduced amounts of adhering albedo. An aqueous solution of a pectinase enzyme is infused into the fruit by a series of positive pressure pulses, and, after then storing the infusion-treated fruit for a prescribed time period, the peel and other membrane material can be readily removed from the fruit and the individual fruit segments readily separated from each other. Infusing the pectinase enzyme solution under pressure, rather than vacuum, and maintaining the solution at approximately room temperature, rather than an elevated temperature, significantly improves the ease of peeling and sectioning and reduces the amount of adhering albedo.

Although the invention has been described in detail with reference to the presently preferred processes, those of ordinary skill in the art will appreciate that various modifications can be made without departing from the invention. Accordingly, the invention is defined only by the following claims.

We claim:

1. A process for preparing peeled fresh citrus fruit, comprising steps of:
   (a) breaking the peel surface of fresh citrus fruit so as to penetrate the albedo layer, but not penetrate the juice sections;
   (b) immersing the fruit in an aqueous solution of pectinase and applying a plurality of positive pressure pulses to the immersed fruit, to infuse the solution into the fruit;
   (c) storing the infusion-treated fruit for a prescribed time period, to allow the pectinase to break down the pectin present in the albedo; and
   (d) removing the peel and other membrane material from the fruit;
   wherein the peeled fruit are free of any substantial amounts of clinging peel and membrane;
   and wherein, when refrigerated, the peeled fruit retain a fresh fruit flavor and appearance for extended durations.

2. A process as defined in claim 1, wherein the citrus fruit are oranges.

3. A process as defined in claim 1, wherein the citrus fruit are grapefruit.

4. A process as defined in claim 1, wherein the citrus fruit are lemons.

5. A process as defined in claim 1, wherein:
   the fresh citrus fruit is maintained at a temperature of about 20 degrees C.;
   the aqueous solution of pectinase has a temperature of about 20 degrees C.; and
   the infusion-treated fruit is stored at a temperature of about 20 degrees C.

6. A process as defined in claim 1, wherein the pressure pulses applied in the step of immersing and applying have pressures of about 20 to 40 p.s.i., relative, and are separated from each other by periods having pressures of about 0 p.s.i., relative.

7. A process as defined in claim 1, wherein the pressure pulses applied in the step of immersing and applying each have durations of about 15 seconds and are separated from each other by periods having durations of about 5 seconds.

8. A process as defined in claim 1, wherein the infusion-treated fruit are stored in the step of storing for about one to two hours prior to the following step of removing.

9. A process as defined in claim 1, and further including a step of repeating steps (a) through (e) on additional fresh citrus fruit using the same batch of an aqueous solution of pectinase as was used initially in the step (b) of pressure infusing.

10. A process as defined in claim 1, wherein the step of breaking includes a step of scoring the peel surface into six substantially equal sections, from stem to blossom end.

11. A process as defined in claim 1, wherein the process is free of any step of artificially heating the fruit or the aqueous solution of pectinase.

12. A process as defined in claim 1, wherein the aqueous solution of pectinase used in the step of infusing has a temperature at or below 26 degrees C.

13. A process as defined in claim 1, and further including a step, following the step of removing, of separating the individual fruit segments from each other, wherein the separate fruit segments have intact membranes that are free of substantial amounts of clinging peel and membrane.

14. A process for preparing individual whole fruit sections from fresh citrus fruit, comprising steps of:
(a) maintaining the core and surface temperatures of fresh citrus fruit at a temperature of about 20 degrees C.;
(b) scoring the peel surface of the fruit so as to penetrate the albedo layer, but not penetrate the juice sections;
(c) immersing the scored fruit in an aqueous solution of pectinase within a pressure chamber, at a temperature of about 20 degrees C., and applying a plurality of pressure pulses to the immersed fruit, the successive pressure pulses each having a pressure of about 20 to 40 p.s.i., relative, and a duration of about 15 seconds and the periods between such pressure pulses each having a pressure of about 0 p.s.i., relative, and a duration of about 5 seconds;
(d) storing the infusion-treated fruit for about one to two hours, at a temperature of about 20 degrees C., to allow the pectinase to break down the pectin present in the albedo;
(e) removing the peel and other membrane material from the fruit;
(f) separating the individual fruit segments from each other; and
(g) repeating steps (a) through (f) on additional fresh citrus fruit using the same batch of an aqueous solution of pectinase as was used initially in the step (c) of immersing and applying;

wherein the separated fruit segments have intact membranes that are free of any substantial amounts of clinging peel and membrane;

and wherein, when refrigerated, the separated fruit segments retain a fresh fruit flavor and appearance for extended durations.

* * * * *